United States Patent
Shinoda et al.

[11] Patent Number: 6,090,910
[45] Date of Patent: *Jul. 18, 2000

[54] DEGRADABLE MONOFILAMENT AND PREPARATION PROCESS THEREOF

[75] Inventors: Hosei Shinoda; Masanobu Ajioka, both of Kanagawa-ken, Japan

[73] Assignee: Mitsui Chemicals, Inc., Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/984,538

[22] Filed: Dec. 3, 1997

[30] Foreign Application Priority Data

Dec. 10, 1996 [JP] Japan ................................ 8-329986

[51] Int. Cl.$^7$ .................... C08G 63/08; C08G 63/88; D02J 1/22; A61L 17/00
[52] U.S. Cl. ................... 528/354; 528/370; 525/415; 523/105; 606/230; 264/290.5
[58] Field of Search ................ 528/354, 370; 525/415; 606/230; 523/105; 264/290.5

[56] References Cited

U.S. PATENT DOCUMENTS 4,700,704 10/1987 Jamiolkowski et al. .
5,252,701 10/1993 Jarrett et al. .
5,747,637 5/1998 Shinoda et al. .......................... 528/354

FOREIGN PATENT DOCUMENTS 1-175855 7/1989 Japan .
6-16792 1/1994 Japan .

OTHER PUBLICATIONS

Bezwada et al, "Monocryl Suture, a New Ultra–Pliable Absorbable Monofilament Suture", *Biomaterials*, 16, (1995), pp. 1141–1148.

*Primary Examiner*—Tae Yoon
*Attorney, Agent, or Firm*—Burns, Doane, Swecker & Mathis, L.L.P.

[57] ABSTRACT

A degradable copolymer filament comprising an internal structure having the following separate phases: (a) a matrix phase comprised as a primary component of a polymer segment which exhibits a tensile Young's modulus of 2 GPa or less and a strength retention of 50% or more after two weeks in water at 37° C., pH 7.3, and (b) a micro-dispersed phase comprised as a primary component of a polymer segment which exhibits a tensile strength of 200 MPa or more and a strength reduction greater than the matrix phase in water at 37° C., pH 7.3. The weight ratio of each component in the matrix phase and dispersed phase is 50:50 to 95:5, respectively, and the dispersed phase a needle structure oriented by stretching in the fiber direction. A degradable monofilament having an excellent mechanical strength and flexibility, moderate hydrolyzability, high ligature stability and being suitable as a material of surgical absorbable suture can be obtained. A preparation process is also provided.

17 Claims, 3 Drawing Sheets

TRANSMISSION TYPE ELECTRON MICROSCOPE PHOTOGRAPH OF
A SECTION PARALLEL TO THE FIBER DIRECTION OF
A MONOFILAMENT OBTAINED IN EXAMPLE 1

TRANSMISSION TYPE ELECTRON MICROSCOPE PHOTOGRAPH OF A SECTION PERPENDICULAR TO THE FIBER DIRECTION OF A MONOFILAMENT OBTAINED IN EXAMPLE 1

TRANSMISSION TYPE ELECTRON MICROSCOPE PHOTOGRAPH OF
A SECTION PARALLEL TO THE FIBER DIRECTION OF
A MONOFILAMENT OBTAINED IN EXAMPLE 4

DEGRADABLE MONOFILAMENT AND PREPARATION PROCESS THEREOF

BACKGROUND OF THE INVENTION

1. Field of the Invention

The present invention relates to a degradable monofilament which has an excellent linear tensile strength, flexibility and moderate degradability at the same time and is excellent in ligature stability (or knot security); a preparation process of the same; and a medical device prepared from said degradable monofilament.

2. Description of the Related Art

Conventionally in a medical field such as surgery, a synthetic absorbable surgical suture has been widely used. Polyglycolic acid (PGA), polylactic acid (PLA) and a glycolic acid/lactic acid copolymer (PLGA) are used for a raw material of the suture. PGA, PLA and PLGA are bioabsorbable polymers and can be degraded in a living body to form degraded products such as lactic acid and glycolic acid. These acids are finally decomposed through a metabolic pathway into carbon dioxide and water, and externally released from the living body. PGA, PLA and PLGA are individually prepared by polymerization of glycolide (GLD) which is a cyclic dimer of glycolic acid, polymerization of lactide (LTD) which is a cyclic dimer of lactic acid, and ring-opening copolymerization of a mixture of GLD and LTD.

PGA and other bioabsorbable polyesters have good processing ability and can provide a high strength filament. On the other hand, the filament has high rigidity and thus a thick monofilament such as a fishing line is very difficult to carry out ligation and is unsuitable for the surgical suture.

Consequently, in the case of preparing the synthetic absorbable surgical suture from PGA or PLGA, many fine filaments are usually spun in order to obtain flexibility, braided, and used as a so-called multifilament. However, the multifilament suture has an irregular surface and leads to a problem of wounding a surrounding tissue of the living body in the course of suture. Further, application of a coating agent is required in order to make the filament slippery in the ligation. Such a treatment renders a manufacturing step complex and economically unfavorable.

In recent years, several monofilament absorbable sutures have been developed in order to overcome the problems noted above.

For example, U.S. Pat. No. 4,700,704 has disclosed a sterilized surgical product which has a sequence on the basis of about 20 to 35 wt % $\epsilon$-caprolactone(CL) and about 65 to 80 wt % GLD, consists of a polymer material having a melting point of 213° C. or less, and has a tensile strength of 30,000 psi or more and a young's modulus of less than 350,000 psi.

Further, a surgical monofilament suture prepared from a copolymer of about 25 mol % CL and about 75 mol % GLD has been described in Biomaterials, Vol. 16, No. 15, pp 1141–1148(1995).

The surgical devices which have been disclosed in these preceding references and prepared from a copolymer of GLD and CL have an excellent flexibility and mechanical strength and thus have an advantage that it is possible to utilize for a surgical suture in the form of monofilament. However, these surgical devices have too high velocity of hydrolysis and quickly decompose in a living body. As a result, it is unsatisfactory to use for a surgical suture and ligation material in the operation of diseased parts having a long recovery period.

Further, the filament above is difficult to make a small and stable knot when ligating with a surgeon's knot in the suture. Thus, the knot is liable to be large and the sutured part tends to become loose. Such a phenomenon is extremely unfavorable in view of the essential object for use of the suture. In order to obtain reliability and safety of ligature, surgeons were required to stabilize the suture by making many knots on the suture.

Japanese Laid-Open Patent HEI 1-175855 has disclosed a stretched surgical monofilament suture consisting of polycaprolactone (PCL) having a relative a viscosity of 2.0 to 8.2. However, degradation and absorption of the PCL suture are very slow in a living body and thus PCL is not practical for an absorbable suture.

Further, U.S. Pat. No. 5,252,701 has disclosed a segmented copolymer having two or more species of different ester bond and exhibiting absorption ability into a living body. The patent has disclosed a segmented copolymer comprising a plurality of fast transesterifying linkages which substantially consists of a glycolate linkage and a plurality of slow transesterifying linkages which is selected from the group consisting of trimethylene carbonate linkages and caproate linkages. The patent has also disclosed a preparation process of the above segmented copolymer wherein two or more species of different cyclic monomers are successively added in two or more steps, a molten copolymer is formed, and the copolymer is further heated to undergo transesterification. The segmented copolymer markedly differs in physical properties from a random copolymer or block copolymer.

However, as shown in the patent specification, the greater the progress of segmentation (transesterification or reshuffling) in the segmented copolymer, the higher the reduction of the melting point and crystallinity of the copolymer. Thus, according to the information of the present inventors, the monofilament prepared from the segmented copolymer does not exhibit sufficient tensile strength for the suture. Similarly, according to the information of the present inventors, low crystallinity of the segmented copolymer leads to too rapid velocity of hydrolysis in a living body. Thus, the segmented copolymer is unsatisfactory to the suture or ligation material for operation of diseased parts requiring a long recovery period.

On the other hand, Japanese Laid-Open Patent HEI 6-16792 has disclosed a preparation process of an CL/GLD copolymer comprising using a polymerization reactor which is equipped with a raw material supply port, copolymer discharge port, exhaust port and stirrer which has excellent surface renewability and is used for the high viscosity solution, forming a low molecular weight oligomer of CL at temperature of 250° C. or less in the first step, adding GLD in the second step and polymerizing at temperature of 100° C. or more, terminating the polymerization reaction by addition of acid anhydride or acid halogenide to the resulting copolymer in the molten state, and successively removing the unreacted monomer with stirring under reduced pressure. However, acid anhydride and acid halide develop peculiar irritating smell even in a trace amount and thus specific design is required for the equipment in the manufacturing factory. Further, it is difficult to completely remove unreacted acid anhydride and acid halogenide from the copolymer, and the resulting copolymer and suture have a disadvantage in smell. The patent specification has no disclosure at all upon the monofilament having flexibility and high strength and the preparation process of the same.

Consequently, one object of the invention is to provide a degradable monofilament which has an outstanding mechanical strength and flexibility, is excellent in ligation stability and has a moderate velocity of hydrolysis, and is suitable for a material of an absorbable surgical suture.

SUMMARY OF THE INVENTION

As a result of an intensive investigation in order to solve the above problems, the present inventors have found in the internal structure of a monofilament that the structure obtained by dispersing a fine needle-like phase comprising as a primary component a polymer segment which exhibits high strength and quick hydrolysis velocity in a matrix comprising as a primary component a polymer segment which is flexible and exhibits slow hydrolysis velocity, can provide a monofilament which in flexible and tough, excellent in ligation stability, and further has a moderate velocity of hydrolysis. The present invention has thus been completed.

That is, one aspect of the invention is a degradable copolymer monofilament comprising an internal structure have the following separate phases: (a) a matrix phase having a polymer segment exhibiting a Young's modulus of 2 GPa or less and a strength retention of 50% or more after two weeks in water at 37° C., pH 7.3, and (b) a microdispersion phase having a polymer segment which exhibits a tensile strength of 200 MPa or more and a strength reduction greater than that of the matrix phase in water at 37° C., pH 7.3, a weight ratio of each component in the matrix phase and the dispersion phase being 50:50 to 95:5, respectively, and the dispersion phase having a needle-like structure oriented by stretching in the fiber direction; a preparation process of the degradable monofilament; and living-body absorbable medical devices prepared from the monofilament.

The term "degradable copolymer" in the invention refers to a copolymer which can decrease in molecular weight in a living body within 5 years by hydrolysis or enzymatic decomposition and be externally discharged by dissolving in water or metabolism. Specific copolymers which can be used include, for example, a copolymer derived from glycolic acid (GA), lactic acid (LA), caprolactone (CL), p-dioxanone (DS), trimethylene carbonate (TMC), ethylene carbonate, hydroxybutyric acid and hydroxyvaleric acid.

The term "internal structure" refers to a concept called morphology among those skilled in the art and polymer researchers, also called morphological structure and used for discussing the type of phase dispersion in multilayer structure.

The term "needle-like structure" refers to an unisotropic structure wherein the axial ratio of the major axis to the minor axis is 3 or more and includes, for example, a circular cylinder, elliptic cylinder, prism, strand, line, string and spindle.

The term "a polymer which has a Young's modulus of 2 GPa or less and a strength retention of 50% or more after immersion in water at 37° C., pH 7.3 for 2 weeks" refers to a polymer which satisfies the below described conditions. That is, a person skilled in the art spins the polymer under suitable conditions and stretches the resulting filament 3 to 10 times. The Young's modulus of the stretched filament thus obtained does not exceed 2 GPa. The filament retains 50% or more in tensile strength after immersion in water at 37° C., pH 7.3 for 2 weeks.

The term "a polymer which has a tensile strength of 200 MPa or more and a strength reduction rate higher than the matrix phase" refers to a polymer which satisfies the below described conditions. That is, a person skilled in the art spins the polymer under suitable conditions and stretches the resulting filament 3 to 10 times. The tensile strength of the stretched filament is 200 MPa or more. The strength retention of the stretched filament is lower than the above low velocity degradable flexible polymer after immersion in water at 37° C., pH 7.3 for 2 weeks.

The internal structure of the monofilament in the invention is divided into a flexible matrix phase having a relatively low degradation velocity and a dispersed phase which exists in the matrix and comprises a needle-like tough structure having a relatively high degradation velocity. The principal component of the matrix phase is a polymer segment which has a Young's modulus of 2 GPa or less and a strength retention of 50% or more after immersion in water at 37° C., pH 7.3 for 2 weeks. The principal component of the dispersed phase is a polymer segment which has a tensile strength of 200 MPa or more and a higher rate of strength reduction as compared with the matrix phase after immersion in water at 37° C., pH 7.3. Further, each component in the matrix phase and dispersed phase is in a weight ratio of 50:50 to 95:5, respectively.

Consequently, the monofilament of the invention simultaneously exhibits a high tensile strength and flexibility and a moderate rate of hydrolysis due to the specific structure consisting of the matrix phase and dispersed phase. That is, the monofilament has a linear tensile strength of 200 MPa or more, Young's modulus (an index of flexibility) of 2.1 GPa or more, and a strength retention of 10 to 80% after immersion in water at 37° C., pH 7.3 for 4 weeks.

As to a preferred internal structure of the degradable monofilament in the invention, the needle-like dispersion phase has 0.5 to 8 μm in the length to fiber direction (major axis) and 0.01 to 0.5 μm in the length of the diameter (minor axis) on a perpendicular section to the fiber axis. The ratio in length of the major axis to the minor axis is in the range of 3 to 20. Deviation can be permitted on the length of major and minor axis and axial ratio. No particular limitation is imposed upon the size of the dispersed phase, even though the size is outside of the above range. However, the proportion of the dispersed phase having a size within the above range is preferably 50% or more, more preferably 70% or more. Most preferably, 70% or more of the needle-like dispersion phase comprises a needle-like portion having 0.01 to 0.5 μm in the diameter (minor axis) of a perpendicular section in a fiber axis and 8 or more in the axial ratio.

The polymer segment which can be used for the principal component of the matrix phase is specifically selected from, for example, polycaprolactone (PCL), poly-p-dioxanone (PDS), poly-trimethylene carbonate (PTMC), a mutual copolymer of the same, and a copolymer of the same with polyglycolic acid (PGA) and polylactic acid (PLA). The PCL segment is preferred.

The polymer segment which can be used for the principal component of the dispersed phase is specifically selected from, for example, PGA, PLA and a mutual copolymer of the same, and a copolymer of the same with PCL, PTMC and PDS. The PGA segment is preferably used.

The polymer segment constituting the principal component of the matrix phase preferably has poor compatibility with the polymer segment constituting the principal component of the dispersed phase.

A suitable aspect of the invention is a degradable monofilament comprising a copolymer of ε-caprolactone (CL) and glycolide (GLD), the internal structure of the monofilament comprises a matrix phase having a polyε-caprolactone (PCL) segment as a principal component and a dispersed phase having a polyglycolic acid (PGA) segment as a principal component, each component of the matrix phase and dispersed phase is respectively in a weight ratio of 50:50 to 95:5, and the dispersed phase comprises a needle-like structure obtained by stretching and orienting the monofilament in the fiber direction (the stretched and oriented monofilament is hereinafter referred to simply as a CG based monofilament).

The CG based monofilament has a structure for reinforcing the filament strength by dispersing and orienting a high strength exerting PGA segment in the fiber direction, and forms a needle-like portion in the matrix of flexible PCL segment. Consequently, the CG based monofilament has flexibility and strength in combination.

The internal structure of the monofilament in the invention can be confirmed, for example, by taking a photograph with a transmission type electron microscope (TEM) at a section in the fiber direction of the monofilament. Specifically, for example, a CG based monofilament is smoothly finished its sectional surface to the fiber direction, dyed with a suitable coloring agent such as ruthenium tetrachloride, and observed under TEM. The matrix phase and dispersed phase can be clearly distinguished due to the difference in dye affinity between PCL and PGA.

In the CG based monofilament of the invention, a small amount of other components can be mixed with the PCL matrix phase and the dispersed PGA phase. However, PCL must be the principal component of the matrix phase and 50 wt % or more PCL is required for the overall matrix phase. Similarly, PGA must be the principal component of the dispersed phase and 50 wt % or more PGA is required for the overall dispersed phase. Exemplary other components which can be mixed in the matrix phase or dispersed phase include, for example, PLA, polydioxanone (PDS), polytrimethylene carbonate (PTMC) and other bioabsorbable polymers, plasticizers, colorants and hydrolysis velocity regulators.

DETAILED DESCRIPTION OF THE PREFERRED EMBODIMENT

Figure 1:
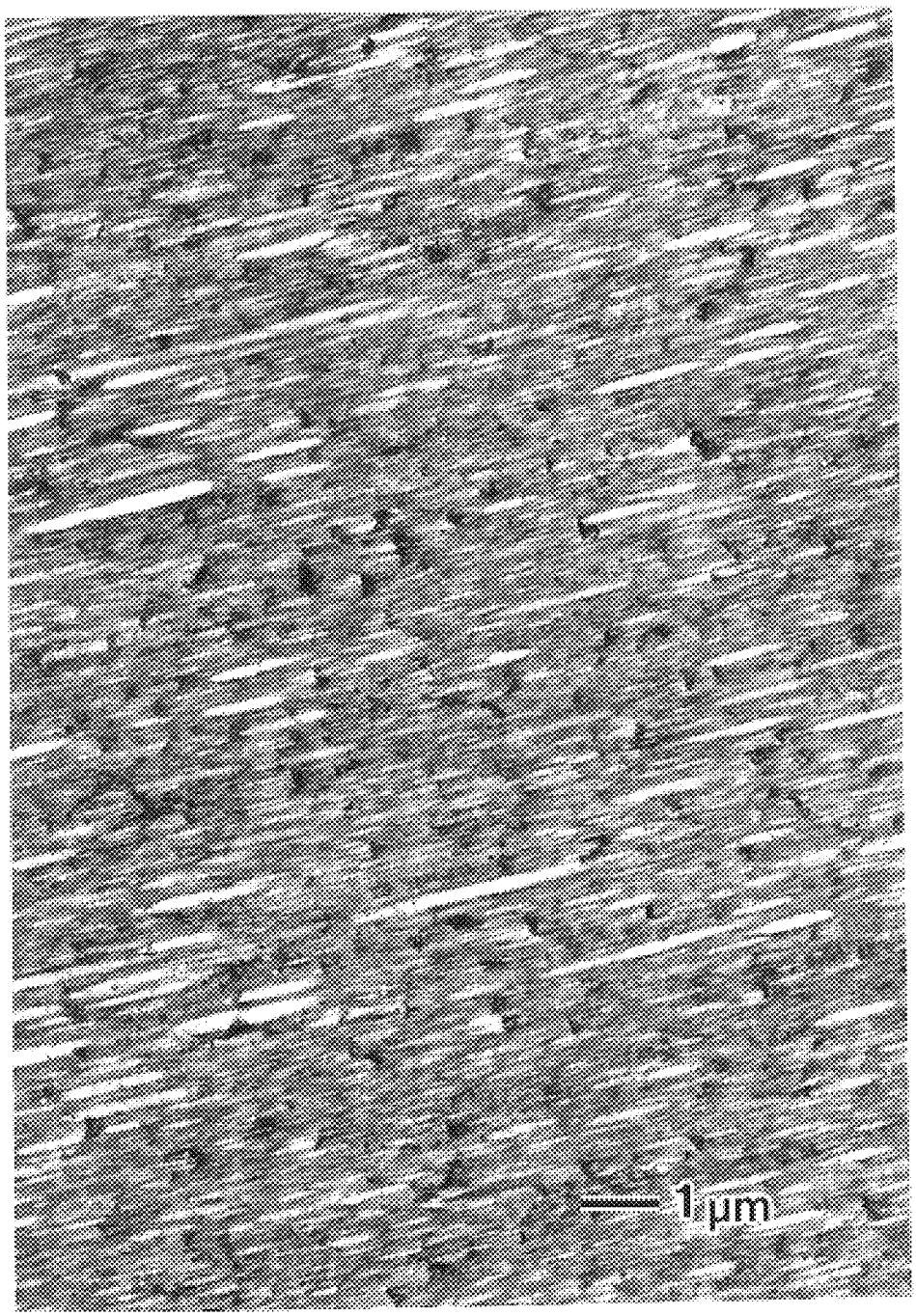
FIG. 1 is a transmission type electron microscope (TEM) photograph of a section parallel to the fiber direction of a monofilament obtained in Example 1.

The present invention will be hereinafter illustrated in detail. The weight average molecular weight (MW) of PCL and PGA can be measured by the method described in the example below.

In the specification, the term poly-ε-caprolactone or PCL does not, unless otherwise noted, refer to a ε-caprolactone (CL) homopolymer alone. Other monomer units in addition to CL units can be copolymerized so long as not greatly impairing the properties of PCL. The amount of copolymerized monomer is 15 mol % or less for the resulting copolymer.

Similarly in the specification, the term polyglycolic acid or PGA does not, unless otherwise noted, refer to a glycolide (GLD) homopolymer alone. Other monomer units in addition to GLD units can be copolymerized so long as not greatly impairing the properties of PGA. The amount of copolymerized monomer is 15 mol % or less for the resulting copolymer. Exemplary other monomer units include, for example, structural units obtained by opening the ring of 1,4-dioxanone (DS), trimethylene carbonate (TM), dioxepanone (DP), LTD, propiolactone (PL), butyrolactone (BL), and valerolactone (VL).

The degradable monofilament of the invention can be suitably prepared by synthesizing a PCL-PGA block copolymer under specific conditions and spinning and stretching the block copolymer under specific conditions.

The degradable monofilament of the invention can be preferably obtained by preparing a AB type or BAB type block copolymer (hereinafter referred to simply as PCL-PGA block copolymer) comprised of a PCL segment (A) and PGA segment (B), melt-spinning the copolymer obtained, and successively stretching the resulting monofilament 3 to 10 times.

The PCL-PGA block copolymer solidifies into the form of filament from the molten state in the spinning step, while constituting the internal structure wherein the phase of PGA segment is dispersed like an island in the matrix phase of PCL segment. In the step, the dispersed phase has not yet formed a needle, though depending upon the spinning conditions, and is in many cases in the form of a sphere or ellipsoid which is slightly distorted to the fiber direction and is less than 3 in the ratio of the major axis to the minor axis. By stretching the unstretched filament under specific conditions, the dispersed phase of PGA segment is stretch-oriented to form a needle.

The PCL-PGA block copolymer used for the degradable monofilament of the invention can be prepared by subjecting 50 to 95 parts by weight of CL to ring-opening polymerization in the presence of a monool compound or a diol compound until the residual CL is reduced to 15 wt % or less, and successively adding 5 to 50 parts by weight of GLD to carry out ring-opening polymerization.

The PCL segment and PGA segment in the PCL-PGA block copolymer used in the monofilament of the invention are preferably homopolymers of CL units and GLD units, respectively. Further, the PCL segment and PGA segment in the PCL-PGA block copolymer used in the monofilament of the invention can be individually copolymerized with other monomer units except CL units and GLD units. However, the amount of other monomer unit must be in the range not greatly impairing the essential properties or PCL and PGA. In view of these points, the amount of other monomer unit is 15 mol % or less for the monomer unit constituting PCL segment or PGA segment. Exemplary other monomer units include, for example, structural units obtained by opening the ring of DS, TMC, DP, LTD, PL, BL and VL.

Control of molecular structure in the PCL-PGA block copolymer is particularly important in the preparation of monofilament by using the PCL-PGA block copolymer. As to the molecular structure of the PCL-PGA block copolymer, the internal structure (morphology) of the monofilament is greatly affected by (i) mol composition ratio of CL units to GLD units (hereinafter referred to simply as PCL/PGA ratio), (ii) weight average molecular weight (MW) of PCL segment, (iii) MW of PGA segment, (iv) MW of PCL-PGA block copolymer, and (v) blocking degree. Consequently, monofilament properties such as strength, flexibility and hydrolysis velocity are remarkably affected by these factors.

(i) The PCL-PGA ratio determines the matrix phase and dispersed phase in the internal structure of the monofilament. Unless PGA composition is smaller than PCL composition, PCL does not form a matrix phase and PGA does not form a dispersed phase in the internal structure of the monofilament. As a substitute, PGA forms a matrix phase and PCL forms a dispersed phase and thus a flexible monofilament cannot be obtained. When the PGA composition is extremely smaller than the PCL composition, it is unfavorable that filament strength is lowered and additionally hydrolysis velocity of the filament becomes extremely slow. In view of these points, the PCL/PGA ratio is preferably in the range of 50:50 to 95:5, more preferably 55:45 to 85:15.

(ii) MW of the PCL segment gives a great influence on the monofilament strength. A certain extent or more MW is required for exerting practical strength as a monofilament. On the other hand, too high MW leads to too high melt viscosity of the polymer and thus processing ability is unfavorably reduced and spinning and stretching become difficult. In view of such circumstance, the range of MW is preferably from 20,000 to 200,000, most preferably from 40,000 to 150,000. The MW used in the specification refers to the weight average molecular weight measured by gel permeation chromatography (GPC) described below.

(iii) MW of the PGA segment affects the size of the dispersed phase in the internal structure of monofilament. Higher MW of the PGA segment increases size of the dispersed phase. The size of the dispersed phase has a profound effect on the physical properties and processability of monofilament. When MW is too high, the PGA phase becomes too large, and particularly high magnification stretching of the filament becomes impossible. As a result, reduction of filament strength or too high velocity of hydrolysis in a living body unfavorably takes place on the contrary. On the other hand, when MW is too low, reinforcing effect on the monofilament cannot be expected for the dispersed phase of the PGA segment. In view of such point, MW of the PGA segment is in the range of preferably 1000 to 200,000, most preferably 4000 to 150,000.

(iv) MW of the PCL-PGA block copolymer affects strength of a monofilament and hydrolysis velocity. When MW is too low, the monofilament does not exert sufficient strength and additionally the strength drops rapidly due to hydrolysis in a living body. On the other hand, too high MW extremely increases melt viscosity of the copolymer and thus troubles occur in the spinning and stretching step. As a result, a good filament is difficult to obtain. In view of such situation, MW of the PCL-PGA block copolymer is preferably in the range of 30,000 to 400,000.

(v) Blocking degree is an index to indicate to what extent each segment is constituted with a single species of structural units in the AB type or BAB type block copolymer having the PCL segment as A block and the PGA segment as B block. In other words, blocking degree is an index to indicate to what extent another CL unit (or GLD unit) is located adjacent to one CL unit (or GLD unit) in a series of structural units of a polymer. For example, an AB type or BAB type block copolymer wherein segment A consists of CL alone and segment B consists of GLD alone has maximum blocking degree. In this case, a CL unit is always located adjacent to a CL unit in the polymer except the connecting point of blocks (AB type has one point and BAB type has two points). For example, when a CL unit is contaminated and copolymerized in the GLD polymer chain of the segment B, blocking degree is reduced with increase in the contaminating proportion of CL and thus the proportion of GLD unit adjacent to the CL unit increases.

The blocking degree of the PCL-PGA block copolymer gives remarkable effect on the phase separation in the internal structure of the monofilament. That is, in the spinning of a copolymer having a high blocking degree, the phase of PGA segment disperses in the matrix of PCL segment in the form of a distinct island structure. Such configuration is elongated in the stretching process to form a needlelike morphology. The monofilament which is the object of the invention and has strength, flexibility and hydrolyzability at the same time can be obtained. With reduction of the blocking degree, phase separation becomes obscure and intermolecular force in the dispersed phase is decreased. Consequently, even though a PCL-PGA block copolymer having a low blocking degree is used for spinning and stretching, the resulting needle-like structure of the PGA segment unfavorably becomes obscure or constitutes a low strength phase, and a monofilament having a high strength can not be obtained.

The blocking degree of the PCL-PGA copolymer can be evaluated by measurement of a $^{13}$C-NMR spectrum. For example, a PCL-PGA block copolymer having a high blocking degree is dissolved in a 2:1 solvent mixture of 1,1,1,3,3,3-hexafluoro-2-propanol (HFP):chloroform deuteride and the $^{13}$C-NMR spectrum is measured. A singlet peak assigned to carbonyl carbon of the GLD unit is observed around 169 ppm and a singlet peak assigned to carbonyl carbon of the CL unit is observed around 178 ppm. Both peaks are individually observed in the form of sharp peak. These peaks coincide completely with the peak which is observed when a GLD homopolymer and CL homopolymer are separately measured by $^{13}$C-NMR under the same condition (these peaks are hereinafter referred to as a homopolymer peak). When a low blocking degree copolymer is subjected to the $^{13}$C-NMR measurement under the same condition, many complex peaks emerge around 169 to 171 ppm and around 176 to 178 ppm in addition to the above homopolymer peaks at 169 ppm and 178 ppm. These complex peaks are assigned to the carbonyl carbon on a caprolactone unit (C) which is shifted by the effect of an adjacent glycolic acid unit (G) like GCC, CCG, and GCG, and the carbonyl carbon on a glycolic acid unit which is shifted by the effect of an adjacent caprolactone unit like CGG, GGC, and CGC. Any of these complex peaks emerge as a result of random configuration and thus these peaks except the homopolymer peak are hereinafter referred to as a random peak.

The PCL-PGA block copolymer used for the degradable monofilament of the invention exhibits substantially no random peak in the $^{13}$C-NMR measurement. Even if the random peak should emerge, the peak intensity assigned to carbonyl carbon in the caprolactone unit adjacent to the glycolic acid unit is about ½ or less, preferably ⅕ or less as compared with the peak intensity assigned to carbonyl carbon in the caprolactone unit adjacent to another caprolactone unit.

A PCL-PGA block copolymer having a high blocking degree exhibits characteristic behavior in differential scanning calorimetry (DSC). That is, endothermal fusion peaks are observed around 50 to 70° C. and around 210 to 240° C. These endothermal peaks almost coincide with melting point of CL homopolymer and GLD homopolymer respectively. When the PCL segment or PGA segment was contaminated with a GLD unit or CL unit, respectively, the block copolymer decreases blocking degree and any of the above two endothermal peaks shift to the low temperature side in the DSC measurement. For example, a block copolymer having a blocking degree lowered to such an extent that a random peak emerged almost equal to a homopolymer peak in the $^{13}$C-NMR measurement, exhibits only one broad endothermal peak around 160 to 200° C. and the endothermal fusion peak assigned to the PCL segment is no longer observed in the low temperature side.

The degradable monofilament of the invention is preferably prepared from the PCL-PGA copolymer exhibiting a distinct endothermal fusion peak around 200 to 240° C. The monofilament obtained by spinning and stretching such PCL-PGA block copolymer has an internal structure comprising a dispersed phase which is definitely composed of the PGA segment and oriented like a needle. The needle-like oriented PGA segment is obtained through orientation and crystallization by stretching and has a relatively sharp endothermal fusion peak around 210 to 240° C. in DSC analysis.

Next, the preferred preparation process of the degradable monofilament in the invention will be illustrated.

The CG-base monofilament which is a suitable embodiment of the invention can be preferably prepared by carrying out ring-opening polymerization of 50 to 95 parts by weight of CL in the presence of a monool compound or diol compound until the residual CL becomes 15% by weight or less, successively adding 5 to 50 parts by weight of GLD and continuing the ring-opening polymerization to obtain a polymer, melting and spinning the polymer at temperature of 220 to 270° C., and stretching the resulting filament 3 to 10 times at temperature of 20 to 80° C.

In the preparation process of the monofilament in the invention, 50 to 95 parts by weight of CL is polymerized to form PCL in the presence of a monool compound or diol compound. The term monool compound or diol compound refers to a compound having one hydroxyl group or two hydroxyl group, and specifically includes, for example, aliphatic alcohol and diol having 1 to 18 carbon atoms. Lauryl alcohol, ethylene glycol and diethylene glycol are preferably used in view of ease in controlling an addition amount and solubility in CL.

The amount of the monool compound or diol compound to be added is suitably determined depending upon the desired molecular weight of the PCL segment, because the molecular weight of PCL can be controlled to some extent by the molar numbers of the monool compound or diol compound. The control method is known by a person skilled in the art. For example, the method disclosed in Japanese Laid-Open Patent HEI 7-233246 (U.S. Pat. No. 5,412,067) can be used. As mentioned above, MW of the PCL segment is an important factor in the structure of the PCL-PGA block copolymer and gives a remarkable effect on the internal structure and physical properties of the degradable monofilament in the invention. In order to control MW of the PCL segment in the above range, the amount of the monool compound or diol compound is preferably selected from the range of 0.01 to 0.5 mol %, more preferably from the range of 0.1 to 0.2 mol %.

Catalysts are preferably used for polymerization of CL. Exemplary polymerization catalysts which can be used include, for example, stannous octoate, tin tetrachloride, zinc chloride, titanium tetrachloride, iron chloride, boron trifluoride ether complex, aluminum chloride, antimony trifluoride, lead oxide and other compound primarily containing a multivalent metal. In these compounds, tin compounds and zinc compounds are preferably used. Stannous octoate is preferred, in particular. The amount of polymerization catalysts is preferably 0.001 to 0.05 wt % for the total amount of CL charged.

Moisture is usually contained in CL used. When CL having a high moisture content is used, it becomes difficult to control MW of formed PCL by adjusting the amount of the monool compound or diol compound. Moisture content is preferably a 1 to 200 ppm. CL is preferably dried, for example, by using a molecular sieve and further distilled to remove moisture.

Further, CL usually contains free hydroxycarboxylic acid such as hydroxycaproic acid. Free hydroxycarboxylic acid gives effect on the molecular weight of the copolymer obtained, and thus the content is as much as possible decreased by distillation or other known methods to a range of preferably 10 to 500 ppm, more preferably 10 to 200 ppm.

Even though polymerization of CL is carried out in the presence of a small amount of other monomers which can copolymerize with CL, the process is still in the scope of the invention. However, the amount of other monomers is 15 mol % or less for CL. Other monomers include, for example, DS, TMC, dioxepanone, GLD, LTD, propiolactone, butyrolactone and valerolactone. Preferred monomers are DS, TMC, LTD and GLD.

Polymerization temperature of CL is preferably 150 to 250° C., more preferably 200 to 235° C., in order to progress polymerization within a short time while inhibiting thermal decomposition of formed PCL.

No particular limitation is imposed upon the polymerization time of CL. However, it is important to carry out polymerization of CL without addition of GLD until the formed PCL attains sufficiently high molecular weight. Polymerization time of CL is preferably in the range of 0.2 to 10 hours in the presence of the above amount of the catalyst in the above temperature range.

In the preparation process of the invention, the residual amount of unreacted CL is preferably reduced to 15 wt % or less at the interval after termination of CL polymerization and before addition of GLD. That is, addition and polymerization of GLD in the presence of 15 wt % or more unreacted CL leads to increase in the proportion of contaminated and copolymerized CL unit in the formed PGA segment. Thus, blocking degree of the PGA segment reduces unfavorably.

More preferably, the amount of residual CL before addition of GLD is 10 wt % or less the amount of GLD. The methods for decreasing unreacted CL in the reaction system before addition of GLD include, for example, 1) a method for enhancing conversion degree of CL to 85% or more by carrying out polymerization of CL under suitable reaction conditions, and 2) a method for removing unreacted CL by heating the reaction system under reduced pressure from the latter half of the polymerization reaction of CL, or at the interval after finishing polymerization and before addition of GLD. The above method 1) can enhance conversion degree to 99% or more and decrease unreacted CL to less than 1% by weight by suitably controlling a catalyst amount, reaction temperature and reaction time. Also the above method 2) can decrease the amount of unreacted CL to less than 1% by weight by suitably controlling temperature, pressure reduction and time during the treatment.

The residual amount of CL before addition of GLD can be evaluated by collecting a small amount of reaction product in the reaction system, dissolving in HFP and measuring by gas chromatography (GC).

In the preparation process of the monofilament in the invention, the PCL-PGA block copolymer or a composition comprising the PCL-PGA block copolymer as a primary component is formed by polymerizing CL, successively adding GLD, and polymerizing GLD.

The amount of GLD is 5 to 50 parts by weight.

The polymerization catalyst can also be added in the polymerization of GLD.

Polymerization of CL in the presence of a hydroxyl compound such as monool and diol provides a hydroxyl terminated PCL. Successive addition and polymerization of GLD leads to growth of a PGA segment from the hydroxyl terminal of PCL to form a PCL-PGA block copolymer. When a monool compound is used in the polymerization of CL, an AB type block copolymer comprised of a PCL segment (A) and PGA segment (B)is formed. When a diol compound is used, a BAB type block copolymer is formed.

It is important to control moisture content of GLD used. The reason is that, in the step of ring-opening polymerization of GLD, presence of moisture leads to polymerization and growth of GLD from positions other than the terminal hydroxyl group of PCL, and enhances proportion of a GLD homopolymer without PCL segment (PGA homopolymer). Increase in the PGA homopolymer formation provides unfavorable effect on the physical properties. Consequently, moisture content of GLD is preferably in the range of 0.1 to 200 ppm. Moisture can be removed from GLD by drying at room temperature to 50° C. under reduced pressure or sludging in a hydrophilic, non-alcoholic, organic solvent which does not dissolve GLD.

Further, GLD usually contains free hydroxycarboxylic acid such as glycolic acid and a chain oligomer of the same. Free hydroxycarboxylic acid is similarly unfavorable because of increase in the proportion of PGA homopolymer formation. The free hydroxycarboxylic acid content in GLD is preferably reduced as much as possible to the range of 10 to 500 ppm, more preferably to the range of 10 to 200 ppm by distillation. recrystallization or sludging.

In the polymerization of GLD, even though a small amount of other monomers is copolymerized with GLD, the process is still in the scope of the invention. However, the amount is 15 mol % or less for GLD. Exemplary other monomers include, for example, DS, TMC, dioxepanone, LTD, propiolactone, butyrolactone, valerolactone, and CL, DS, TMC, LTD and CL are preferred.

When the polymerization temperature of GLD is too low, formed PGA segment crystallizes and forms rubber-like solid in the reactor and additionally the reaction progresses non-uniformly. Thus, the filament having desired properties cannot be obtained. On the other hand, too high polymerization temperature unfavorably tends to cause heat decomposition of the PGA segment. In view of these points, polymerization temperature is preferably in the range of about 200 to 250° C. It is usually preferred to carry out the polymerization in nitrogen or other inert atmosphere.

PCL formed by the polymerization of CL before addition of GLD has a molecular weight of preferably in the range of 20,000 to 200,000, more preferably 150,000 or less. When the molecular weight of PCL is too high, melt viscosity of PCL becomes too high in the above temperature range of GLD polymerization. Consequently, uniform dispersion of GLD in PCL becomes difficult and a specific stirring unit is required.

No particular restriction is imposed upon the addition method of GLD to the reaction system. However, polymerization product of CL has a high viscosity in the molten state, whereas added GLD forms molten liquid of low viscosity in the reaction system. Consequently, when a large amount of GLD is added at a time to the reaction system, GLD and PCL cannot be mixed satisfactorily and the reaction is liable to be non-uniform. The phenomenon makes addition of the PGA segment to the terminal of PCL chain non-uniform, enhances proportion of PGA homopolymer formation, and renders exhibition of favorable properties impossible. Consequently, preferred addition method of GLD is to add prescribed amount of GLD continuously or intermittently by small portions so as to limit the amount of GLD addition per minute within 20% by weight of CL used.

The polymer obtained by polymerization of GLD comprises unreacted GLD or CL. These unreacted materials render hydrolysis velocity of a monofilament quicker than desired, and thus their content is preferably reduced as much as possible. The content of residual GLD or CL is preferably less than 5 wt %, more preferably less than 1 wt % for the amount of GLD or CL used, respectively. Consequently, polymerization of GLD is preferably carried out until a conversion rate of 95% or more is obtained.

When the polymerization time of GLD is too short, the conversion of GLD is unfavorably insufficient. On the other hand, when the polymerization time of GLD is too long, blocking degree is unfavorably impaired, since transesterification reaction between formed PGA segment and PCL segment gradually progresses. In view of this point, polymerization time is preferably 0.2 to 5 hours, more preferably 0.3 to 3 hours in the range of the above polymerization temperature.

When polymerization of GLD is carried out at the above polymerization time, transesterification reaction between PGA segment and PCL segment does not substantially occur and blocking degree of the block copolymer is not extremely impaired.

No particular limitation is imposed upon the polymerization time of GLD. However, the polymerization time until a conversion rate of 95 wt % is attained is usually 0.2 to 5 hours in the above temperature range.

The conversion degree of GLD can be measured by gas chromatography similarly to the conversion degree of CL.

The unreacted monomer is preferably removed from the polymer obtained by reducing the pressure in the molten state as intact or by cooling, crushing and successively heating under reduced pressure. In the case of removing the unreacted monomer under reduced pressure in the molten state as intact, deaeration is carried out at 200 to 240° C. by finally reducing the pressure to 13,300 Pa or less over 0.2 to 1 hour and maintaining said condition for 0.3 to 2 hours. The pressure is preferably reduced to 130 Pa.

Further, in the case of removing the unreacted monomer by cooling, crushing and successively heating the polymer under reduced pressure, the copolymer is preferably in the form of powder, pellet or other fine particles. Deaeration is preferably carried out at 20 to 60° C. under reduced pressure of 13,300 Pa or less for 0.5 to 72 hours. The pressure is preferably reduced to 130 Pa. Both methods can be carried out with or without stirring.

In the preparation process of the monofilament in the invention, the above obtained polymer is melt spun into a filament and successively stretched.

Melt spinning is carried out in the range of 220 to 270° C. When the spinning temperature is too low, fusion of the PGA segment is unsatisfactory and thus delivery of a spun filament becomes unstable or formation of the PGA dispersed phase in the internal structure of a monofilament becomes obscure or unsuitable. As a result, the desired monofilament-having a high strength and flexibility and moderate hydrolyzability in combination cannot be obtained.

Melt spinning is preferably carried out with a twin-screw extruder. The PCL-PGA block copolymer which is suitably used for the invention is liable to form a rubber-like in the range of 60 to 200° C. When a single-screw extruder which is usually employed by those skilled in the art is used, the rubber-like copolymer wraps around the screw around the feeding port and makes delivery of the monofilament difficult. A kneader type, screw type and other types of twin-screw extruders can be used.

Further, in the melt spinning step, the filament extruded from a spinning nozzle is preferably cooled within 1 to 30 seconds from delivery by immersing in a cooling medium at −100 to 50° C. When a longer time is elapsed in the interval from delivery to cooling, crystallization of the PGA dispersed phase in the filament proceeds in excess and stretching in the next step becomes difficult to carry out uniformly and satisfactorily under prescribed conditions. As a result, the desired degradable monofilament having a high strength and flexibility and moderate hydrolyzability in combination cannot be obtained. The cooling medium which can be used are water, hydrocarbon compounds, alcohol, inert gas such as nitrogen, air and argon and other known materials.

The filament obtained by spinning is stretched 3 to 10 times at 20 to 80° C. When the stretching temperature is too low, uniform stretching of overall filament is impossible, the matrix phase alone is stretched in particular, a needle-like PGA dispersed phase is difficult to form, and thus good properties cannot be expected for the resulting filament. On the other hand, when the stretching temperature is too high, the filament breaks in the course of stretching or good orientation of the filament and dispersed phase cannot be obtained, and thus strength reduction of the filament unfavorably tends to occur on the contrary. Stretching must be carried out in the above range of temperature in order to provide good stretching for the dispersed phase and inhibit filament breakage. Particularly preferred stretching temperature is in the range of 40 to 70° C.

Further, when stretching magnification (or drawing ratio) is too low. sufficient orientation cannot be provided for both the PCL matrix and PGA dispersed phase and thus satisfactory strength of the filament cannot be obtained. Additionally, the PGA dispersed phase cannot form a satisfactory needle-like structure and thus the filament is liable to cause shortage in flexibility. On the other hand, too high stretching magnification leads to stretching breakage or destruction of internal structure and results in lowering of strength or shortage in flexibility on the contrary.

No particular limitation is imposed upon the size of the degradable monofilament in the invention. The monofilament has a diameter of usually 0.005 to 2 mm, preferably 0.02 to 1 mm.

The degradable monofilament of the invention has a linear tensile strength of 200 MPa or more, a ligature tensile strength 170 MPa or more, and a Young's modulus of 2.1 GPa or less. Hydrolyzability, that is, residual ratio of a linear tensile strength (proportion to the original tensile strength) after immersion in water at 37° C. pH 7.3 for 4 weeks is usually 10 to 80%, 20 to 70% in a preferred embodiment, 30 to 70% in a more preferred embodiment.

The present invention can provide a degradable monofilament and a preparation process of the same, a monofilament which has an excellent mechanical strength and flexibility, moderate hydrolyzability, and high ligature stability and is suited for a material of surgical absorbable suture.

The degradable monofilament of the invention exhibits a high linear tensile strength and ligature tensile strength, sufficient flexibility and moderate hydrolyzability as mentioned above and can be applied to various portions of a living body.

Further, the degradable monofilament of the invention has a good ligature stability and a knot does not become loose when it is made once. On the other hand, any of the conventionally known monofilament suture is liable to form a large knot and has poor knot stability (ligature stability). Consequently, surgeons were required to stabilize the ligature by making many knots on the suture. The monofilament of the invention can provide a small and stable knot with ease and ligature stability can be sufficiently obtained by making only one knot.

Generally, a knotted filament has a lower tensile strength than an unknotted filament. It has been known that, when the conventional monofilament is knotted, the tensile strength (ligature tensile strength) is decreased to 50 to 60% of the original tensile strength (linear tensile strength). The tendency becomes more remarkable with increasing numbers of the knot.

On the other hand, the ligature strength of the monofilament in the invention merely decreases to 70 to 80% of the linear tensile strength and additionally, as mentioned above, ligature can be stabilized with a smaller numbers of knots as compared with the conventional monofilament. Consequently, satisfactory ligature strength can be insured when practically applying to an operation and is very advantageous in view of safety insurance on the operation.

No particular restriction is imposed upon the uses of the degradable monofilament in the invention. For example, the monofilament can also be used as a material for a fishing line. Preferred applications are formed items for medical devices.

The degradable monofilament of the invention can be processed into medical molded articles or devices by known methods. Exemplary medical articles include a monofilament suture, bone reinforcement plate, surgery net and slow release medicine.

No particular restriction is imposed upon the preparation process of the monofilament suture. Known processes can be utilized and dying, coating, needling, sterilization and packaging can be applied, when necessary.

EXAMPLE

The present invention will be hereinafter illustrated further in detail by way of examples. In these examples, the molecular weight of PGA, PCL and PCL-PGA block copolymer, conversion degree of CL and GLD, composition of copolymer, blocking degree, melting point of copolymer, linear tensile strength, Young's modulus, residual ratio of linear tensile strength after hydrolysis and ligature stability were measured and evaluated by the following methods.

(1) Molecular Weight (MW) of PGA, PCL and PCL-PGA Block Copolymer

A solution having a concentration of about 0.2 wt % was prepared by dissolving the polymer in HFP. The solution was measured by gel permeation chromatography using a model:GPC:SYSTEM 21(hereinafter referred to as GPC), manufactured by SHOWA-DENKO Co. A weight average molecular weight (MW) was calculated from polymethyl methacrylate as reference.

(2) Conversion Degree of CL and GLD

Formed polymer was dissolved in HFP, and the content of CL and GLD in the polymer (amount of residual monomer) was measured by capillary gas chromatography. Conversion degree was calculated from the content.

(3) PCL/PGA Composition (part by weight) of Copolymer

A solvent mixture of HFP and chloroform deuteride was used in a volume ratio:HFP/CDCl$_3$=2:1. The copolymer was dissolved in the solvent mixture at a concentration of 5 wt %. A nuclear magnetic resonance apparatus, model:FX-90Q manufactured by NIPPON DENSHI Co. was used for the measurement. A spectrum was measured on the nucleus-H in the range of 1 to 9 ppm. Ratio of each component (part by weight) in the sample was obtained from each resonance intensity of a methylene group assigned to a CL unit (2.4 ppm) and a methylene group assigned to a GLD unit (4.8 ppm). Hereinafter referred to as $^1$H-NMR analysis.

(4) Evaluation of Blocking Degree

An HFP/CDCl$_3$ solution of the polymer was prepared by the same procedures as above (3). A spectrum was measured on the nucleus-C in the range of 160 to 190 ppm by using the nuclear magnetic resonance apparatus. Hereinafter referred to as $^{13}$C-NMR analysis.

(5) Melting Point of Copolymer (° C.)

A differential scanning calorimeter (DSC). Model:DSC-8230, manufactured by RIGAKU Co. was used.

Melting point of a copolymer was measured by operating at a heating rate of 10° C. per minute.

(6) TEM Observation

A filament was embedded into a six-hour curing type two-component epoxy resin and smoothly exposed by cross-section of the sample by cutting with a glass knife of ultra-microtome and dyed with ruthenium tetrachloride for about 15 hours. After washing, an ultra thin specimen having a thickness of about 70 nm was cut out with a diamond knife of the ultra-microtome and observed by using in electron microscope, TEM model:H 7000, manufactured by HITACHI Co, at accelerating voltage of 75 kv.

Additionally, it was confirmed that PCL was more strongly dyed with ruthenium tetrachloride than polyglycolic acid from the TEM observation results on each simple substance specimen of PGA and PCL.

(7) Linear Tensile Strength (MPa) and Young's modulus (GPa)

Measurement was carried out with a tensile tester at a chuck width of 40 mm and pulling rate of 100 mm/min in accordance with JIS L-1069. Linear tensile strength was calculated from a maximum load (N) before breakage of the sample. Young's modulus was calculated from the slope of a stress (load)-strain curve in the initial, linear elastic region according to the following equation.

Young's modulus=(tan θ×L·C·S)/(H×A)

where θ is an angle(°) of the initial linear portion of the stress-strain curve with the strain axis(X-axis), L is chuck width(mm). C is chart speed(mm/min), S is load per graduation of the strain axis(N/mm). H is pulling rate(mm/min), and A is sectional area of the sample(mm$^2$).

(8) Ligature Tensile Strength(MPa)

A surgeon's knot was applied twice to the monofilament sample and a tensile test was carried out by the same procedures as (7) linear tensile strength. Calculated from a Maximum Load Before Breakage.

(9) Residual Ratio of Linear Tensile strength after hydrolysis (%)

A monofilament sample was immersed in a phosphate buffer solution at 37° C., pH 7.27 for prescribed period. After drying the sample, a linear tensile strength was measured according to the method described in (7). The residual ratio is shown by the percentage(%) of the strength after immersion for the original strength before immersion.

(10) Ligature Stability

A monofilament sample was wrapped twice on a glass tube having a diameter of 20 mm so as to bring into a close contact with the tube surface, and a surgeon's knot was made. Thereafter the sample was allowed to stand at 23° C. under relative humidity of 50% for 24 hours. The time dependent change on the state of the increase of looseness of the knot was visually observed.

The ligature stability of the sample was evaluated by the grade of loosened state of the knot on the glass tube.

Evaluation standard was as follows.

Rank A:Knot had no looseness and was in close contact with the glass tube.

Rank B:Knot become loose and still adhered to the glass tube.

Rank C:Knot become greatly loosed and separated from the glass tube.

Reference Example 1

Polyε-caprolactone(PCL) having MW of 60,000 was spun at 110° C. and stretched 7 times on a hot plate maintained at 50° C. to obtain a PCL monofilament having a diameter of 0.4 mm. The monofilament had a linear tensile strength of 380 MPa and a Young's modulus of 0.9 GPa. The residual ratio of tensile strength after hydrolysis was 93% after 2 weeks, 87% after 4 weeks.

Reference Example 2

Polyglycolic acid (PGA) having MW of 50,000 was spun at 250° C. and stretched to a maximum stretching magnification (4.5 times) on a hot plate maintained at 50° C. to obtain a PGA monofilament having a diameter of 0.5 mm. The monofilament had a linear tensile strength of 970 MPa and a Young's modulus of 14.7 GPa. The residual ratio of tensile strength after hydrolysis was 76% after 2 weeks, 15% after 4 weeks. The filament was rigid and a knot was difficult to form.

Example 1

CL used was previously dried for 3 days with 3A type molecular sieve and distilled. CL had a moisture content of 75 ppm.

GLD used was previously repeated recrystallization from ethyl acetate and dried overnight at 40° C. under reduced pressure. GLD had a moisture content of 30 ppm.

To a 5 liter reactor which was equipped with a mechanical stirrer, dropping funnel having a heating unit, and reduced pressure deaeration device and was previously dried by heating under reduced pressure, 60 parts by weight of CL, 0.015 wt % of stannous octoate for CL, and 0.132 mol % of lauryl alcohol for CL were charged.

After ventilating nitrogen in the reactor for 5 minutes, the reaction mixture was heated to 220° C. over 20 minutes in the nitrogen atmosphere as intact and maintained the same temperature for 2 hours. At the stage, conversion degree of CL to the polymer was 98% and the resulting PCL had MW of 56,000.

Successively, 40 parts by weight of GLD was charged to the dropping funnel, fused by heating to 110° C., continuously added into the reactor over 10 minutes and vigorously stirred for 5 minutes. Thereafter reaction temperature was raised to 235° C. with moderate stirring and the temperature was maintained for an hour. The conversion rate of GLD to the copolymer was 99 wt %. The pressure in the reactor was gradually reduced to remove unreacted monomer. The copolymer thus obtained had a PCL/PGA composition of 61/39 and MW of 98,000.

A $^{13}$C-NMR spectrum of the resulting copolymer was measured in the range of 160 to 190 ppm. A peak assigned to carbonyl carbon of the GLD unit was found at 168.7 ppm, and a peak assigned to carbonyl carbon of the CL unit was found at 177.8 ppm. Both peaks emerged singly and sharply, and other random peak was not observed.

Further, a melting point of the resulting copolymer was measured with a differential scanning calorimeter. The copolymer had distinct melting points due to heat absorption which indicate peaks at 56° C. and 219° C.

Next, the copolymer thus obtained was spun at a maximum temperature of 250° C. with a twin screw extruder fitted with a spinning nozzle having a single hole of 2.5 mm in an internal diameter. An ice-water bath of 0° C. was set at 15 cm below the extruding nozzle so as to immerse the delivered filament into the ice water bath after 3 seconds from extrusion. The filament was passed through the ice water bath for 20 seconds and wound up. The filament obtained was stretched 7.4 times while sliding on a hot plate at 63° C. to obtain a stretched monofilament having a diameter of 0.45 mm.

Figure 2:
FIG. 2 is a TEM photograph of a section perpendicular to the fiber direction of a monofilament obtained in Example 1.

FIG. 1 and FIG. 2 illustrate TEM photographs showing section parallel to the fiber direction and a section perpendicular to the fiber direction of the monofilament obtained, respectively. It was confirmed that a PGA phase which was difficultly dyed with a staining agent was dispersed in a needle-like oriented state in the fiber direction in a PCL matrix which was dyed black with the staining agent.

According to the image analysis of TEM photographs, the PCL phase and PGA phase had an area ratio of 65/35. The PGA dispersed phase had a length of the major axis of 0.1 to 5 μm, length of the minor axis of 0.01 to 0.3 μm, and an axial ratio of 5 to 20. More than 90% of the needle-like dispersed phase had an axial ratio of 8 or more.

The monofilament obtained had a linear tensile strength of 480 MPa, Young's modulus of 1.3 GPa, ligature tensile strength of 380 MPa, and residual ratio of strength after hydrolysis was 55%. The result of ligature stability evaluation was rank A.

Example 2

The same procedures as described in Example 1 by using 60 parts by weight of CL except that lauryl alcohol was substituted with diethylene glycol in an amount of 0.132 mol % for CL.

The conversion degree of CL to the copolymer was 98%. PCL formed had MW of 59,000.

Successively, 40 parts by weight GLD was added and polymerization was carried out by the same procedures as Example 1. The conversion degree of GLD to the copolymer was 99 wt %. The copolymer obtained had a PCL/PGA composition of 59/41, and MW of 101,000.

A $^{13}$C-NMR spectrum of the resulting copolymer was measured in the range of 160 to 190 ppm. A peak assigned to carbonyl carbon of the GLD unit was found at 168.7 ppm, and a peak assigned to carbonyl carbon of the CL unit was found at 177.8 ppm. Both peaks emerged singly and sharply, and other random peak was not observed.

Further, a melting point of the resulting copolymer was measured with a differential scanning calorimeter. The copolymer had distinct melting points due to heat absorption which indicate peaks at 56° C. and 219° C.

Next, the copolymer thus obtained was spun by the same procedures as Example 1 at a maximum temperature of 250° C. with a twin screw extruder mounted with a single hole spinning nozzle. An ice-water bath of 0° C. was set at 15 cm below the extruding nozzle so as to immerse the delivered filament into the ice water bath after 4 seconds from extrusion. The filament was passed through the ice water bath for 20 seconds and wound up. The filament obtained was stretched 6.9 times while sliding on a hot plate at 63° C. to obtain a stretched filament having a diameter of 0.49 mm.

The monofilament obtained was observed with a TEM at a section parallel to the fiber direction and a section perpendicular to the fiber direction. It was confirmed that a PGA phase which was difficultly dyed with a staining agent was dispersed in a needle-like oriented state to the fiber direction in a PCL matrix which was dyed black with the staining agent. According to the image analysis of TEM photographs, the area ratio of the PCL phase to the PGA phase was 65:35. The PGA dispersed phase had 0.05 to 5 μm in the length of the major axis and 0.01 to 0.3 μm in the length of the minor axis and 5 to 20 in the axial ratio. More than 90% of the needle-like dispersed phase had an axial ratio of 8 or more.

The monofilament obtained had a linear tensile strength of 520 MPa, Young's modulus of 1.1 GPa, ligature tensile strength of 370 MPa, and residual ratio of strength after hydrolysis for 4 weeks was 48%. The result of ligature stability evaluation was rank A.

Example 3

A copolymer was prepared by carrying out polymerization of CL and polymerization of GLD similarly to Example 1 except that 75 parts by weight of CL and 25 parts by weight of GLD were used.

The conversion degree of CL to the copolymer was 98 wt %, and formed PCL had a MW of 83,000. The conversion degree of GLD to the copolymer was 99 wt %.

The copolymer obtained had a PCL/PGA composition of 75/25 and a MW of 111,000.

A $^{13}$C-NMR spectrum of the resulting copolymer was measured in the range of 160 to 190 ppm. A peak assigned to carbonyl carbon of the GLD unit was found at 168.7 ppm, and a peak assigned to carbonyl carbon of the CL unit was found at 177.8 ppm. Both peaks emerged singly and sharply, and other random peak was not observed.

Further, a melting point of the resulting copolymer was measured with a differential scanning calorimeter. The copolymer had distinct melting points due to heat absorption which indicate peaks at 55° C. and 216° C.

Next, the copolymer thus obtained was spun by the same procedures as Example 1 at a maximum temperature of 250° C. with a twin screw extruder equipped with a spinning nozzle having a single hole of 2.5 mm in an internal diameter. An ice-water bath was set at 15 cm below the extruding nozzle so as to immerse the delivered filament into the ice water bath after 7 seconds from extrusion. The filament was passed through the ice water bath for 20 seconds and wound up. The filament obtained was stretched 7.8 times while sliding on a hot plate at 60° C. to obtain a stretched monofilament having a diameter of 0.41 mm.

The stretched monofilament thus obtained was observed under TEM at a section parallel to the fiber direction and a section perpendicular to the fiber direction. It was confirmed that a PGA phase which was difficultly dyed with a staining agent was dispersed in a needle-like oriented state to the fiber direction in a PCL matrix which was dyed black with the staining agent. According to the image analysis of TEM photographs, the area ratio of the PCL phase to the PGA phase was 78:22. The length of the major axis and minor axis of the PGA dispersed phase was a 0.1 to 5 μm and 0.01 to 0.3 μm, respectively. The axial ratio of the PGA dispersed phase was 5 to 20. Afore than 90% of the needle-like dispersed phase had an axial ratio of 8 or more.

The monofilament obtained had a linear tensile strength of 460 MPa, Young's modulus of 1.0 GPa, ligature tensile strength of 360 MPa, and residual strength ratio after hydrolysis for 4 weeks was 65%. Result of ligature stability evaluation was rank A.

Comparative Example 1

A copolymer was prepared by carrying out polymerization of CL and polymerization of GLD similarly to Example 1 except that 40 parts by weight of CL and 60 parts by weight of GLD were used.

The conversion degree of CL to the polymer was 95 wt %, and formed PCL had a MW of 51,000. The conversion degree of GLD to the copolymer was 99 wt %.

The copolymer obtained had a PCL/PGA composition of 41/59 and A MW of 109,000.

A $^{13}$C-NMR spectrum of the resulting copolymer was measured in the range of 160 to 190 ppm. A peak assigned to carbonyl carbon of the GLD unit was found at 168.7 ppm, and a peak assigned to carbonyl carbon of the CL unit was found at 177.8 ppm. Both peaks emerged singly and sharply, and other random peak was not observed.

Further, a melting point of the resulting copolymer was measured with a differential scanning calorimeter. The copolymer had distinct melting points due to heat absorption which indicate peaks at 55° C. and 220° C.

Next, the copolymer thus obtained was spun by carrying out the same procedures as Example 1 with a twin screw extruder equipped with a spinning nozzle having a single hole of 2.5 mm in an internal diameter. The resulting filament was rigid. Various species of stretching were tried at 40 to 80° C. However, a maximum stretching magnification obtained was 4.5 times. Filament breakage occurred frequently when the stretching magnification was further increased.

A section of the monofilament obtained was observed under TEM. The matrix was constituted by the PGA phase which was difficultly dyed with the staining agent, and the PCL phase irregularly dispersed in a PGA matrix.

The monofilament obtained had a linear tensile strength of 410 MPa, Young's modulus of 4.4 GPa, ligature tensile strength of 260 MPa, and residual strength ratio after hydrolysis for 4 weeks was 5%. The filament was rigid. The result of ligature stability evaluation was rank C.

Comparative Example 2

After throughly mixing 60 parts by weight of CL and 40 parts by weight of GLD, the same amount of stannous octoate and lauryl alcohol as used in Example 1 were added to the mixture and polymerized by heating similarly to Example 1. Polymerization progressed slowly and it took 7 hours before finishing polymerization. After terminating polymerization, the reactor was gradually evacuated to remove unreacted residual monomer. The copolymer obtained had a PCL/PGA composition of 62/38 and a MW of 97,000.

A $^{13}$C-NMR spectrum of the copolymer obtained was measured in the range of 160 to 190 ppm. A peak assigned to carbonyl carbon of the GLD unit was found at 168.7 ppm, and a peak assigned to carbonyl carbon of the CL unit was found at 177.8 ppm. However, in addition to these peaks, random peaks emerged at 168.8, 168.9, 169.6, 169.8, 169.9, 170.8, 176.4, 176.5 and 177.6 ppm. The random peaks of the CL unit had an intensity 3 times of the homopolymer peaks.

Further, a melting point of the copolymer obtained was measured with a differential scanning calorimeter. A broad endothermal peak was merely found at 170 to 200° C. and no heat-absorption peak was found around 50 to 70° C. and around 210 to 240° C.

Next, the copolymer thus obtained was spun by carrying out the same procedures as Example 1 with a twin screw extruder equipped with a spinning nozzle having a single hole of 2.5 mm in an internal diameter.

The filament obtained was stretched 7 times by sliding on a hot plate at 63° C. to obtain a stretched filament having a diameter of 0.45 mm.

The stretched monofilament was observed under TEM at a section parallel to the fiber direction and a section perpendicular to the fiber direction. However, in any of these sections, the whole portion was lightly and uniformly dyed and the structure of phase separation could not be observed.

The monofilament obtained had a linear tensile strength of 150 MPa, Young's modulus of 1.0 GPa. ligature tensile strength of 100 MPa and residual strength ratio after hydrolysis for 4 weeks was 5%. The filament was flexible, but had low tensile strength and quick hydrolysis velocity and thus was not practical for uses such as surgical suture. Ligature stability was rank B.

Comparative Example 3

Polymerization was carried out by the same procedures as Example 1 except that GLD addition was carried out without removing the unreacted CL out of the reaction system when the conversion degree in the CL polymerization reached to 70%. The formed PCL before addition of GLD had a MW of 42,000.

After finishing polymerization of GLD, the reactor was gradually evacuated to remove the unreacted, residual monomer. The copolymer obtained had a PCL/PGA composition of 63/37 and a MW of 102,000.

A $^{13}$C-NMR spectrum of the copolymer obtained was measured in the range of 160 to 190 ppm. A peak assigned to carbonyl carbon of the GLD unit was found at 168.7 ppm, and a peak assigned to carbonyl carbon of the CL unit was found at 177.8 ppm. However, in addition to these peaks, random peaks emerged at 168.8, 168.9, 169.6, 169.8, 169.9, 170.8, 176.4, 176.5 and 177.6 ppm. The random peaks of the CL unit had almost the same intensity as the homopolymer peaks.

Further, a melting point of the copolymer obtained was measured with a differential scanning calorimeter. A broad endothermal peak was found at 170 to 200° C. No heat-absorption peak was found around 210 to 240° C.

Next, the copolymer thus obtained was spun by the same procedures as described in Example 1 with a twin screw extruder fitted with a spinning nozzle having a single hole of 2.5 mm in an internal diameter.

The monofilament obtained was stretched 7.0 times by sliding on a hot plate at 63° C. to obtain a monofilament having a diameter of 0.46 mm.

The stretched monofilament was observed under TEM at a section parallel to the fiber direction and a section perpendicular to the fiber direction. However, in any of these sections, the whole portion was lightly and uniformly dyed and the structure of separated phase could not be found.

The monofilament obtained had a linear tensile strength of 220 MPa. Young's modulus of 1.3 GPa, ligature tensile strength of 160 MPa and residual strength ratio after hydrolysis for 4 weeks was 15%. The filament was flexible, whereas had low tensile strength and quick hydrolysis velocity and thus was not practical for uses such as surgical suture. Ligature stability was rank B.

Example 4

A PCL-PGA block copolymer was prepared spun and stretched by the same procedures as Example 1 except that stretching was carried out at room temperature (15° C.). The stretching magnification was 4.4 times at the maximum.

Figure 3:
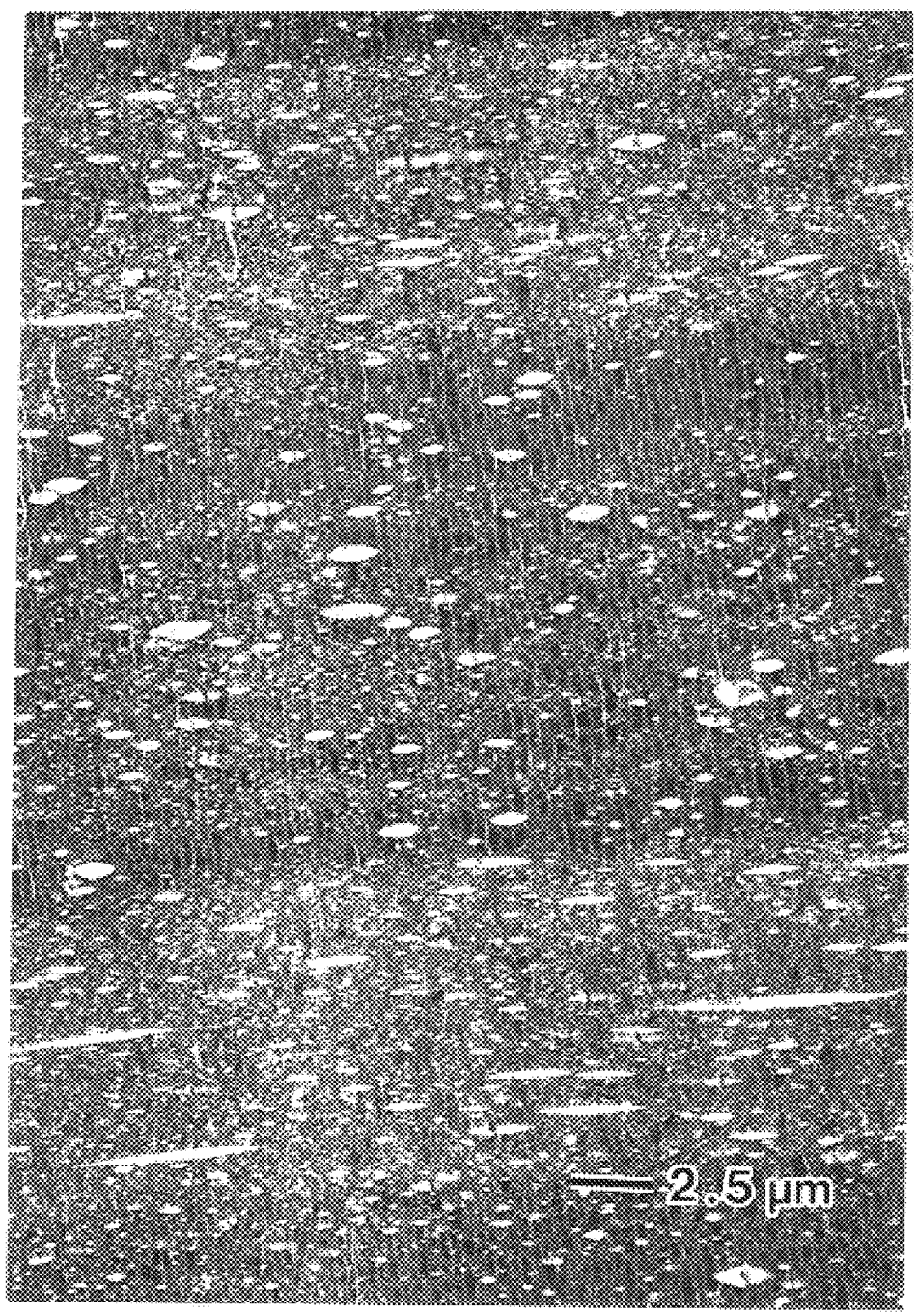
FIG. 3 is a TEM photograph of a section parallel to the fiber direction of a monofilament obtained in Example 4.

FIG. 3 illustrates TEM photograph of a section parallel to the fiber direction of the monofilament obtained. A PGA phase which was difficultly dyed with a staining agent was dispersed in a PCL matrix which was dyed black with the staining agent. However a needle-like dispersed phase and an island (spherical) dispersed phase were present and thus non-uniform stretching was proved. According to the image analysis of TEM photographs, the proportion of needle-like dispersed phase having an axial ratio of 3 or more was 40%.

The stretched monofilament obtained had a linear tensile strength of 330 MPa, Young's modulus of 1.6 GPa, ligature tensile strength of 22 MPa and residual strength ratio after hydrolysis for 4 weeks was 45%. Result of ligature stability evaluation was rank A.

Comparative Example 4

For reference, a GLD/CL copolymer was prepared by the process disclosed in U.S. Pat. No. 4,700,704.

To a 5 liter reactor equipped with a mechanical stirrer, dropping funnel having a heating unit, and reduced pressure deaeration system and previously dried under reduced pressure, 856 g of CL, 508 g of GLD, 12.5 ml of toluene solution containing 0.033 mol/l of stannous octoate, and 5.9 g of hexandiol were charged.

After ventilating nitrogen into the reactor for 5 minutes, the reaction mixture was heated to 190° C. over 20 minutes in the nitrogen atmosphere as intact and maintained the temperature for an hours.

Successively, 1524 g of GLD was charged to the dropping funnel, fused by heating to 110° C. and added with stirring to the reactor which was maintained at 190° C. Thereafter, the reaction mixture was heated to 205° C. and stirred for 6 hours. The conversion degree was 95 wt %.

The PCL/PGA copolymer thus obtained had PCL/PGA composition of 25/75 and a MIW of 94,000.

A $^{13}$C-NMR spectrum of the copolymer obtained was measured in the range of 160 to 190 ppm. A peak assigned to carbonyl carbon of the GLD unit was found at 168.7 ppm, and a peak assigned to carbonyl carbon of the CL unit was found at 177.8 ppm. However, in addition to these two peaks, random peaks emerged at 168.8, 168.9, 169.6, 169.8, 169.9, 170.8, 176.4, 176.5 and 177.6 ppm. The random peaks had an intensity 6 times of the homopolymer peaks.

Further, a melting point of the copolymer obtained was measured with a differential scanning calorimeter. The copolymer had a melting point indicating broad absorption of heat in 155 to 206° C.

Next, the copolymer obtained was spun with a twin screw extruder (PLASTOMILL, manufactured by TOYO SEIKI Co.) equipped with a spinning nozzle having a single hole of 2.5 mm in an internal diameter. The maximum spinning temperature was 230° C. An ice water bath of 0° C. was set at 15 cm below the extruding nozzle so as to immerse the delivered filament into the ice water bath after 7 seconds from extrusion. The filament was passed through the ice water bath for 20 seconds and wound up. The filament obtained was stretched at the maximum stretching magnification of 6 times while sliding on a hot plate at 63° C. to obtain a stretched monofilament having a diameter of 0.55 mm.

The stretched monofilament was observed under TEM at a section parallel to the fiber direction and a section perpendicular to the fiber direction. However, in any of these sections, the whole portion was lightly and uniformly dyed, and the structure of separated phase could not be found.

The stretched monofilament obtained had a linear tensile strength of 400 MPa. Young's modulus of 1.1 GPa, and ligature tensile strength of 220MPa. Residual strength ratio after hydrolysis for 4 weeks was 0%. The filament obtained was flexible and had a high linear tensile strength. However, hydrolysis velocity was high, and thus use of the filament as a suture was limited to the operation requiring a short ligation period. Result of ligature stability evaluation was rank B and the ligature stability was poor.

What is claimed is:

1. A degradable copolymer monofilament consisting of an internal structure having the following separate phases:
    (a) a matrix phase having a polymer segment exhibiting a Young's modulus of 2 GPa or less and a strength retention of 50% or more after two weeks in water at 37° C., pH 7.3, and
    (b) a micro-dispersion phase having a polymer segment which exhibits a tensile strength of 200 MPa or more and a strength reduction greater than that of the matrix phase in water at 37° C., pH 7.3,
    a weight ratio of each component in the matrix phase and the dispersion phase being 50:50 to 95:5, respectively, and the dispersion phase having a needle structure oriented by stretching in the monofilament direction wherein the matrix phase is a poly(ε-caprolactone) and the dispersed phase is a polyglycolic acid.

2. The degradable monofilament according to claim 1, wherein 70% or more of the dispersed phase has a needle structure oriented in the monofilament direction.

3. The degradable monofilament according to claim 2, wherein the needle structure oriented in the monofilament direction has a diameter of 0.01 to 0.5 μm on a perpendicular section to the monofilament axis and a ratio of the major axis to the minor axis of 8 or more.

4. The degradable monofilament according to claim 1, wherein 70% or more of the dispersed phase has a needle structure oriented in the monofilament direction, the perpendicular section of the monofilament axis has a diameter of 0.01 to 0.5 μm and a ratio of the major axis to the minor axis of 8 or more.

5. The degradable monofilament according to claim 1, wherein the matrix phase or the dispersed phase indicates a distinct heat absorption in 210 to 240° C. on a differential scanning calorimeter.

6. The degradable monofilament according to claim 1, wherein the degradable monofilament is obtained by subjecting 50 to 95 parts by weight of ε-caprolactone to ring-opening polymerization in the presence of a monool compound or a diol compound, decreasing the residual caprolactone to 15% by weight or less, successively adding 5 to 50 parts by weight of glycolide, carrying out ring-opening polymerization to prepare a AB or a BAB block copolymer consisting of a poly(ε-caprolactone) segment (A) and a polyglycolic acid segment (B), melt-spinning said block copolymer, and stretching the resulting filament 3 to 10 times.

7. The degradable monofilament according to claim 6, wherein the poly(ε-caprolactone) segment has a weight average molecular weight of 40,000 to 150,000.

8. The degradable monofilament according to claim 6, wherein the polyglycolic acid segment has a weight average molecular weight of 1,000 to 200,000.

9. The degradable monofilament according to claim 6, wherein the block copolymer has a weight average molecular weight of 30,000 to 400,000.

10. The degradable monofilament according to claim 6, wherein the block copolymer has a high blocking degree and a $^{13}$C-NMR spectrum exhibits a ½ or less intensity in the peak assigned to carbonyl carbon of a caprolactone unit adjacent to glycolic acid unit as compared with the peak assigned to carbonyl carbon of caprolactone unit adjacent to caprolactone.

11. A process for preparing a degradable monofilament according to claim 1, wherein the degradable monofilaments obtained by subjecting 50 to 95 parts by weight of ε-caprolactone to ring-opening polymerization in the presence of a monool compound or a diol compound, until the weight average molecular weight of formed poly(ε-caprolactone) reaches to 20,000 to 200,000, decreasing the residual caprolactone to 15% by weight or less, successively adding 5 to 50 parts by weight of glycolide, carrying out ring-opening polymerization to prepare a copolymer, melt-spinning the copolymer at 220 to 270° C., and stretching the resulting filament 3 to 10 times.

12. The process for preparing a degradable monofilament according to claim 11, wherein glycolide is continuously or intermittently added at a rate per minute of not exceeding 20% by weight of ε-caprolactone used.

13. The process for preparing a degradable monofilament according to claim 11, wherein glycolide is added, when the weight average molecular weight of poly(ε-caprolactone) reaches to 40,000 to 150,000 in the caprolactone polymerization.

14. The process for preparing a degradable monofilament according to claim 11, wherein, in the melt-spinning, a filament delivered from a spinning nozzle is immersed within 1 to 30 seconds from extrusion in a cooling medium maintained at −100 to 50° C.

15. The process for preparing a degradable monofilament according to claim 11, wherein the stretching is carried out at 20 to 80° C.

16. A bioabsorbable medical device prepared from the degradable monofilament according to claim 1.

17. A bioabsorbable medical device according to claim 16, wherein the bioabsorbable medical device is a monofilament suture.

* * * * *